United States Patent [19]

Murase et al.

[11] Patent Number: 4,466,943
[45] Date of Patent: Aug. 21, 1984

[54] FLAME PHOTOMETRIC DETECTOR ANALYZER

[75] Inventors: Isao Murase; Katsutoshi Hirose, both of Yokosuka, Japan

[73] Assignee: Nissan Motor Co., Ltd., Yokohama, Japan

[21] Appl. No.: 210,496

[22] Filed: Nov. 26, 1980

[30] Foreign Application Priority Data

Nov. 28, 1979 [JP] Japan .................................. 54-153040
Nov. 28, 1979 [JP] Japan .................................. 54-153041
Dec. 25, 1979 [JP] Japan .................................. 54-167633

[51] Int. Cl.$^3$ ..................... G01N 21/72; G01N 33/00; G01N 31/08
[52] U.S. Cl. .................................. 422/91; 356/315; 422/54; 422/80; 422/89; 436/171
[58] Field of Search ................... 422/80, 89, 91, 94; 356/307, 315, 417; 23/232 B; 436/171

[56] References Cited

U.S. PATENT DOCUMENTS

| | | | |
|---|---|---|---|
| 3,695,813 | 10/1972 | Griffith | 356/315 |
| 3,743,425 | 7/1973 | Jobe | 356/315 |
| 3,837,808 | 9/1974 | Sugimoto et al. | 23/232 E |
| 3,960,495 | 6/1976 | Tantram | 422/97 |

FOREIGN PATENT DOCUMENTS

| | | |
|---|---|---|
| 55-62343 | 5/1980 | Japan .................................. 356/417 |
| 599190 | 3/1948 | United Kingdom . |
| 712700 | 7/1954 | United Kingdom . |
| 946689 | 1/1964 | United Kingdom . |
| 957212 | 5/1964 | United Kingdom . |
| 963030 | 7/1964 | United Kingdom . |
| 1326448 | 6/1971 | United Kingdom . |

OTHER PUBLICATIONS

Analytical Chemistry 49, 1977, pp. 126-128.

Primary Examiner—Michael S. Marcus
Attorney, Agent, or Firm—Schwartz, Jeffery, Schwaab, Mack, Blumenthal & Koch

[57] ABSTRACT

A flame detector analyzer of the type wherein a sample gas is introduced into a flame formed by burning a fuel gas in presence of a combustion supporting gas, comprises a background providing device for supplying a background component gas capable of emitting a characteristic spectrum having the same wave length as that of the characteristic spectrum of a measuring object component contained in the sample gas, the light spectrums emitted from the measuring object component and the background component gas being received and treated to be detected, thereby increasing the measuring accuracy for the measuring object component and improving the resolving power at a low concentration detection region.

16 Claims, 21 Drawing Figures

FLAME PHOTOMETRIC DETECTOR ANALYZER

BACKGROUND OF THE INVENTION

1. Field of the Invention

This invention relates to improvements in a flame photometric detector analyzer for analyzing a component in a sample gas, and more particularly to an improvement in the precision thereof.

2. Description of the Prior Art

Flame photometric detector analyzers are now in common use, for example, as relative spectroscopic detector analyzers, particularly for the analysis of sulfur and phosphoric substances. The basic elements of the flame photometric detector analyzer includes a burner jet where a sample gas is burned in the combustion chamber provided by hydrogen fuel gas and a combustion supporting gas such as oxygen or air, and a spectrophotometer for observing the burning sample gas, including a suitable light filter and photodetector. When a measuring object component or substance containing sulfur in the sample gas is burned in a hydrogen rich flame by introducing the sample gas into or in the vicinity of the hydrogen rich flame, the measuring object component emits a characteristic light spectrum. The intensity (or luminous intensity) of the light spectrum is electronically detected to quantitatively analyze the concentration of the measuring object component.

BRIEF SUMMARY OF THE INVENTION

According to one aspect of the present invention, a flame photometric detector of the type wherein a sample gas is introduced into a flame which is formed, under supply of a combustion supporting gas, at the tip of a burner jet to which a fuel gas is supplied, comprises a background providing device for supplying a background component gas which is capable of emitting a characteristic light spectrum having the same wave length as that of the characteristic spectrum of a measuring object component contained in the sample gas, when being supplied to the flame. The light spectrums emitted from the measuring object component and the background component are received and treated in order to be detected. With this arrangement, the detected value of the background component gas is added to the detected value of the measuring object component, and therefore the measuring accuracy of the measuring object component is greatly improved and the resolving power at a low concentration detection region is greatly improved, thereby extending the lower concentration detection limit for the measuring object component in the sample gas.

In another aspect of the present invention, the flame photometric detector further comprises a device for reducing oxide materials or interference materials contained in the sample gas to be introduced into the flame, the device including a reduction catalyst for promoting the reduction reaction of the oxide materials. With this catalyst device, the interference materials can be effectively converted into non-interference materials, and therefore the luminous intensity of the measuring object component is never interfered from the oxide materials contained in the sample gas, thereby exhibiting a detected value which very precisely corresponds to the concentration of the measuring object component in the sample gas.

In a further aspect of the present invention, the flame photometric detector analyzer further comprises a device for decreasing the density of oxide materials or interference materials contained in the sample gas to be introduced into the flame, whereby the density of the sample gas is decreased by thermally expanding the volume thereof or by reducing the pressure in a combustion chamber in which the flame is formed. With this density decreasing device, the interference effect due to the interference materials can be suppressed, thereby improving the detection accuracy for the measuring object contained in the sample gas.

In a still further aspect of the present invention, the flame photometric detector analyzer further comprises a first device for supplying a standard gas into the flame which standard gas has a certain concentration of a component and capable of generating a dark current to be detectable, a second device for supplying an interference gas into the flame, which interference gas is capable of varying the dark current, and a third device for controlling the pressure of the sample gas to be introduced into the flame with reference to the variation of the dark current, to regulate the amount of the sample gas to be supplied to the flame. With this additional arrangement, the checking and adjusting of the flow amount of the sample gas to be supplied to the flame can be easily achieved by sensing the variation of the dark current upon supplying the interference gas, thereby enabling precise adjustment of the flow amount of the sample gas to be supplied to the flame without troublesome flow amount checking and adjustment operations which have been necessary in conventional flame photometric detector analyzers.

BRIEF DESCRIPTION OF THE DRAWINGS

The features and advantages of the flame photometric detector analyzer according to the present invention will be more clearly appreciated from the following description taken in conjunction with the accompanying drawings in which like reference numerals designate the corresponding parts and elements, and in which.

DETAILED DESCRIPTION OF THE INVENTION

Figure 1:
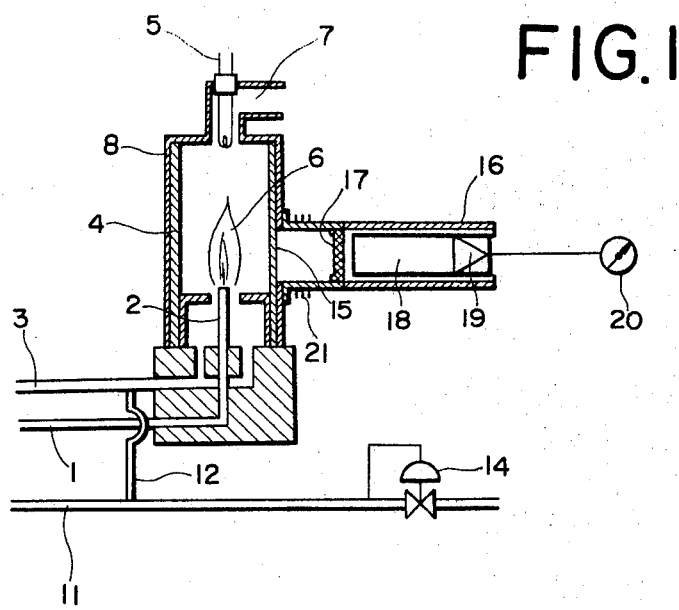
FIG. 1 is a diagrammatic sectional view of a conventional flame photometric detector analyzer.

To facilitate understanding the present invention, a brief reference will be made to a conventional flame photometric detector analyzer, depicted in FIG. 1. Referring to FIG. 1, hydrogen gas supplied via a hydrogen gas supply line 1 to a hydrogen gas nozzle 2 or burner jet is mixed with air supplied via a combustion supporting gas (air) supply line 3 and then ignited by a suitable flame igniter 5 to be burned within a quartz glass cylinder 4 to form a hydrogen rich flame 6. The quartz glass cylinder 4 is disposed in a casing 8 provided with an exhaust port 7.

A sample gas (e.g., automotive exhaust gas) containing a component (e.g., $SO_2$ gas) to be measured flows continuously through a sample supply line 11. The sample gas flowing in the line 11 is introduced via a branched sample introduction line 12 to the combustion supporting gas line 3, so that the sample gas is mixed with combustion supporting air, and then supplied in its mixed state into or in the vicinity of the hydrogen rich flame 6. The supply amount of the sample gas is regulated by a pressure regulating device 14 disposed in the sample supply line 11 downstream of the sample introduction line 12.

Figure 2:
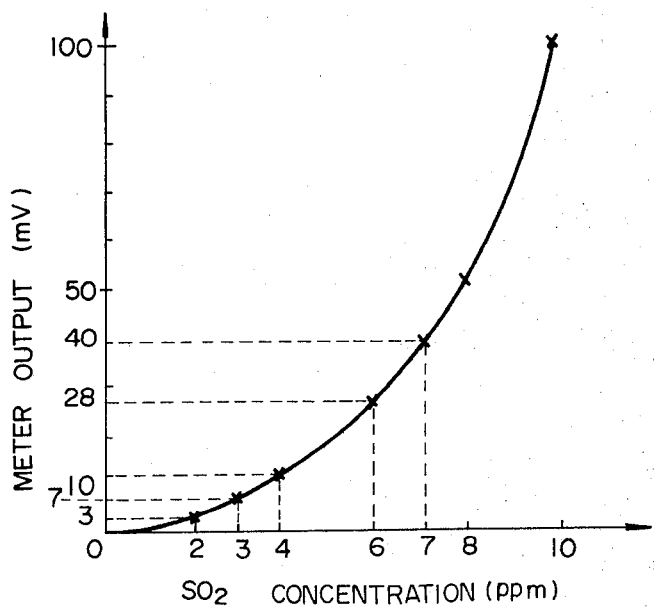
FIG. 2 is a graph showing an identification curve for a measuring object component in terms of the concentration of the component.

The measuring object component of the sample gas introduced into the hydrogen rich flame emits a characteristic light spectrum which is introduced to a narrow-band optical filter 17 disposed inside a cover 16 through a window 15 formed in the wall of the casing 8. Here, only the characteristic light spectrum of the measuring object component passes the optical filter 17 and then is caught by a photomultiplier tube 18 to convert the light spectrum to an electric signal. The electric signal is supplied via an amplifier 19 to a voltmeter 20 for detecting the characteristic light spectrum intensity as the value of a voltage level. It will be understood that the intensity of the light spectrum caught by the photomultiplier tube 18 has a certain relationship with the concentration of the measuring object component, and therefore it is possible to quantitatively analyze the unknown concentration of the measuring object component. An example of such a relationship is shown in FIG. 2. In FIG. 1, the reference numeral 21 designates cooling fins for facilitating heat emission therefrom.

With such a conventional flame photometric detector analyzer, as indicated by the identification curve in FIG. 2, the variation rate of the output of the voltmeter decreases as the concentration of the measuring object component ($SO_2$) decreases. Besides, the identification line exhibits parabolic characteristics. These contribute to the degradation in analytical accuracy of the measuring object component at low concentration range.

Figure 3:
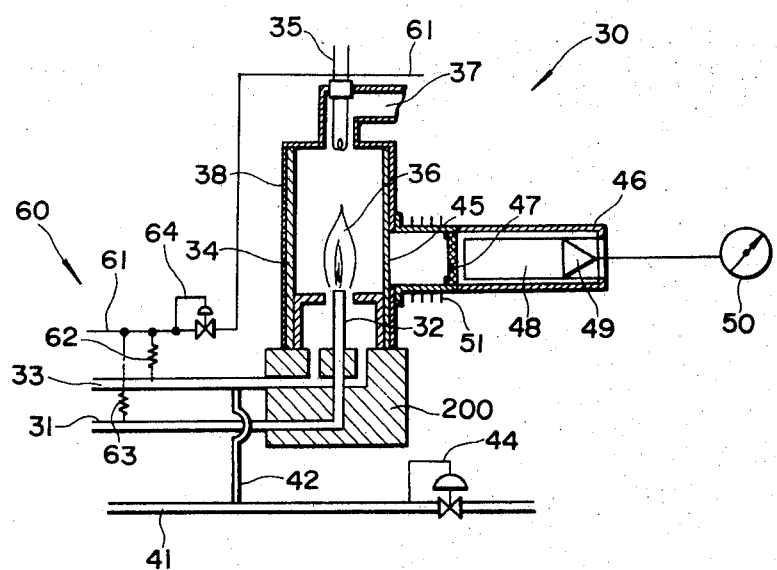
FIG. 3 is a diagrammatic sectional view of a first embodiment of a flame photometric detector analyzer in accordance with the present invention.

In view of the above description of the conventional flame photometric detector analyzer, reference is now made to FIG. 3 wherein a first embodiment of a flame photometric detector (FPD) analyzer according to the present invention is illustrated by the reference numeral 30. The analyzer 30 comprises a quartz glass cylinder 34 defining therein a combustion chamber (no numeral). The quartz glass cylinder 34 is disposed within a casing 38 having an exhaust outlet 37. A hydrogen gas nozzle or burner jet 32 projects into the combustion chamber, which nozzle is connected to a hydrogen gas supply line 31, a part of which is located in a base member 200 to which the casing 38 is secured. Additionally, a combustion supporting gas (air) supply line 33 is provided to supply air to the vicinity of the tip of the hydrogen gas nozzle 32. As shown, a part of the combustion supporting gas line 33 is formed through the base member. A sample supply line 41 is provided so that a sample gas (automotive exhaust gas in this instance) containing a component ($SO_2$) to be analyzed or measured flows therethrough. A sample gas introduction line 42 branches off from the sample supply line 41 and is connected to the combustion supporting gas line 33, so that the sample gas is mixed with air flowing therein. A pressure regulating device 44 is disposed in the sample supply line upstream of the sample introduction line in order to regulate the supply amount of the sample gas to the combustion supporting gas supply line 33.

A background providing device 60 is provided to supply, into the hydrogen gas supply line 31 or the combustion supporting gas supply line 31, a component or substance (having a certain concentration) which emits the characteristic light spectrum having the same wave length as that of the characteristic light spectrum of the measuring object component in the sample gas when introduced into a hydrogen rich flame. Such a component or substance is hereinafter referred to "a background component". Accordingly, the background providing device 60 includes a background component gas supply line 61. The background component gas flowing through the line 61 is introduced through respective metering pipes 62 and 63 to the combustion supporting gas supply line 33 and the hydrogen gas supply line 33. A pressure regulator 64 is disposed in the background component gas supply line 61 upstream of the metering pipes 62 and 63, in order to regulate the supply amount of the background component gas to a certain value. While a certain concentration of the same component or substance as the measuring object component has been selected in the above as the background component, it will be appreciated that the background component is not limited to such a component, and accordingly other components may be used as the background component.

A suitable igniter 35 is disposed to project into the combustion chamber formed within the quartz glass cylinder, to ignite the hydrogen gas mixture from the hydrogen nozzle 32 and the combustion supporting gas supply line 33, so that hydrogen rich flame 36 is formed.

A narrow-band optical filter 47 is disposed in a cover 46 to receive the light from the flame 36 through a window 45 formed in the casing 38. The cover 46 is formed with cooling fins 51 on the outer surface thereof and in the vicinity of the casing 38. A photomultiplier tube 48 is disposed in the cover 46 to catch light spectrum passed through the optical filter 47 and convert the spectrum into an electric signal representing the luminous intensity of the spectrum. The photomultiplier tube 48 is electrically connected through an amplifier 49 to a voltmeter 50, so that the luminous intensity of the light spectrum is detected as a voltage value.

With the thus arranged flame photometric detector analyzer, when the background component gas is supplied from the background providing device 60 into the combustion supporting gas line 62 and the hydrogen gas supply line 31 and is carried into the hydrogen rich flame 36, the background component emits a constant level of light spectrum which has the same wave length as that of the light spectrum from the measuring object component. The thus emitted characteristic spectrum from the background component and the measuring object component passes through the optical filter 47 and is then detected as a voltage level by the voltmeter 50. It will be understood that the detected voltage level is the sum of the values corresponding to the measuring object and the background component.

The effect gained by the above-mentioned flame photometric detector analyzer will be exemplified also with reference to FIG. 2. FIG. 2 is an empirical graph of the relationship between the $SO_2$ concentration and voltage output in a device arranged as shown in FIG. 1. As shown, a 2 ppm $SO_2$ concentration results in a voltmeter 20 output of 3 mV, and a 3 ppm $SO_2$ concentration (an increase of 1 ppm) results in an output of 7 mV. The slope of the curve increases as the $SO_2$ concentration increases, so that at higher concentration increases, an increase of 1 ppm (e.g. from 6 ppm (28 mV) to 7 ppm (40 mV)), results in a greater difference in output voltage (40 mV−28 bV=12 mV). Therefore, at higher $SO_2$ concentration levels, the meter output voltage resolution increases. The present invention shifts the range of $SO_2$ concentration up to a range where the output voltage resolution is greatly increased in order to more accurately detect slight variations in $SO_2$ concentration in the measuring object component.

In the example given above, when 4 ppm of $SO_2$ is supplied as the background component, a change from 2 to 3 ppm in the measuring object component is read as a change from 6 to 7 ppm. Therefore, the meter 20 reads a difference of 12 mV (40 mV@7 ppm−28 mV@6 ppm) rather than a difference of 4 mV (7 mV@3 ppm−3 mV@2 ppm). This demonstrates the fact that the resolution in the case of supplying also the background component is much greater than that in the conventional case of supplying only the measuring object component.

Thus, according to the present invention, the voltage output at a low concentration region as in the identification curve in FIG. 2 is raised by a certain level corresponding to a predetermined concentration, thereby improving the detection resolution. This greatly improves the reading accuracy of the flame photometric detector analyzer, thereby greatly extending the limit of the concentration of the measuring object component supplied to the detector. It will be understood that the background component cancels itself in calculating the difference and accordingly the voltmeter output corresponding to it is zero.

Figure 4:
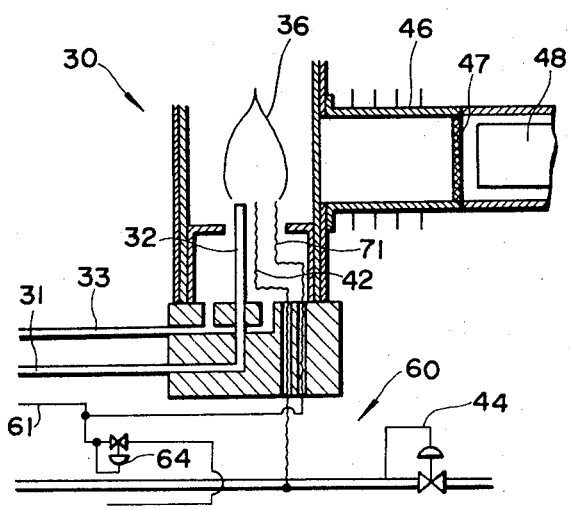
FIG. 4 is a diagrammatic sectional view similar to FIG. 3 showing a modified example of the analyzer of FIG. 3.

FIG. 4 shows a modified example of the embodiment of FIG. 3, in which both the sample gas and the background component are directly supplied into the hydrogen rich flame 36 instead of being supplied with the air and hydrogen gas. In FIG. 4, the sample introduction line 42 branches off from the sample supply line 41 and extends to the vicinity of the tip of the hydrogen nozzle 32, so that the sample gas is directly introduced into the hydrogen rich flame 36. Additionally, a background component gas introduction line 71 branches off from the background component gas supply line 61 and extends to the vicinity of the tip of the hydrogen nozzle 32, so that the background component gas is directly introduced into the hydrogen rich flame 36. The tip sections of the sample gas introduction and background component gas introduction lines 42,71 form capillary tubes.

In the above-discussed instances, the sample gas is exhaust gas from an automotive internal combustion engine whose operation mode is continuously varied, in which the background component is $SO_2$. Therefore, it has been apparent that a noxious component, $SO_2$, in the exhaust gas can be continuously quantitatively analyzed with high accuracy.

As discussed above, according to the present invention the flame photometric detector analyzer is equipped with the background providing device for supplying to the hydrogen rich flame the component or substance which emits the characteristic light spectrum having the same wave length as that of the measuring object component. Therefore, the measuring accuracy of the object component is greatly improved and additionally the resolving power at a low concentration region is greatly improved, thereby extending the lower concentration limit for detection.

Figure 5:
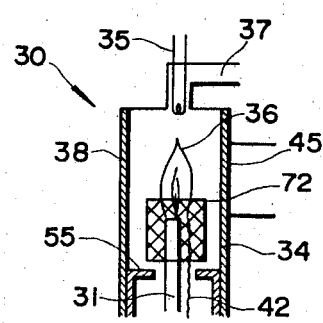
FIG. 5 is a schematic sectional view of an essential part of the second embodiment of a flame photometric detector analyzer in accordance with the present invention.

FIG. 5 illustrates a part of a second embodiment of the flame photometric detector analyzer 30 in accordance with the present invention. In this embodiment, the analyzer 30 is provided with a cylindrical catalyst 72 positioned around the tip sections of the hydrogen nozzle 32 and the sample gas introduction line or capillary tube 42. The cylindrical catalyst 72 contains a catalytic material which promotes the reduction of exhaust gas oxide components such as CO, $CO_2$ and NO which coexist with the measuring object component in the sample gas or the exhaust gas. The catalytic material is, for example, Ni or its alloy, platinum, or rhodium. The reference numeral 55 designates an air guide.

With this arrangement, when the sample gas (exhaust gas in this instance) is discharged from the capillary tube 42, light producing material such as $SO_x$ and $S_x$ in the sample gas produces flame light upon contacting the hydrogen rich flame 36. Then, the combustion supporting gas having a lower oxygen concentration such as about 11 to 16% is supplied via the combustion supporting gas supply line 33, and therefore hydrogen excessive reduction atmosphere is formed around the flame 36, so that the coexisting components such as CO, $CO_2$ and NO are effectively reduced in the presence of the catalyst 72. As a result, the components CO, $CO_2$ and NO are converted into $CH_4$, $CH_4$ and $N_2$, respectively.

Figure 6:
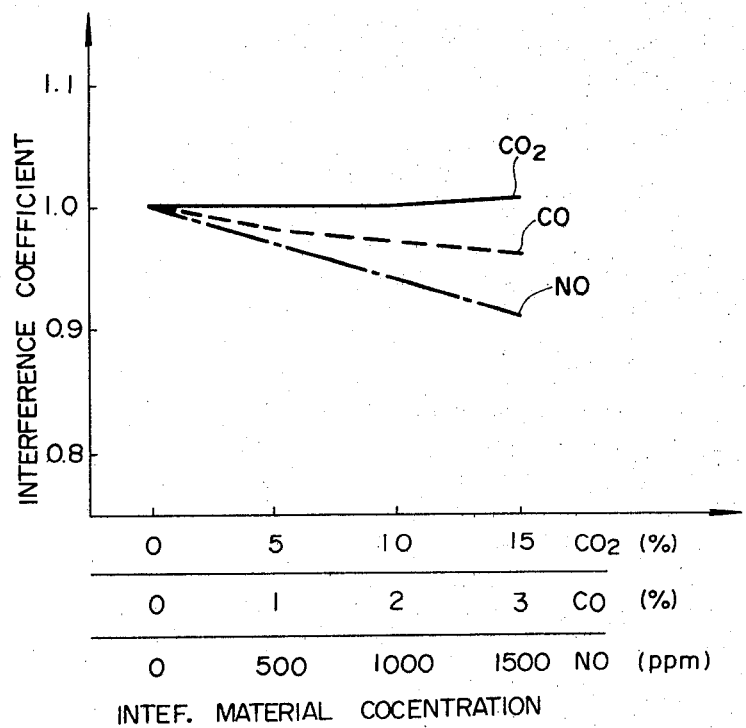
FIG. 6 is a graph showing the interference coefficient of interference components to the luminous intensity of the measuring object component, in terms of the concentration of the interference components.

The advantageous effect of this embodiment will be discussed hereinafter in comparison with the conventional flame photometric detector analyzer. Since the sample gas, such as automotive exhaust gas, contains $CO_2$, CO, and NO other than the measuring object component such as $SO_2$, such oxides or interference components greatly contribute to the voltmeter output in the above-mentioned conventional analyzer. The interference coefficients of CO and NO decrease (see FIG. 6) with the increased concentration of the interference components, and the interference coefficient of $CO_2$ increases slightly with the concentration increase. This interference coefficient means the increase or decrease rate of the meter output under the action of the interference component, assuming that the meter output due to the luminous intensity of a pure S and its compound is 1.0. FIG. 6 demonstrates that CO and NO contribute to decrease the luminous intensity, thereby lowering the meter output, while $CO_2$ allows the meter output to increase slightly. In this regard, it has been proposed to decrease the oxygen concentration in the air supplied from the combustion supporting gas supply line to a level, for example, of 11 to 16%. This results in the hydrogen discharged from the hydrogen nozzle 2 burning under a hydrogen excessive condition, and accordingly the hydrogen burning flame produces a reduction atmosphere, thereby slightly suppressing the effect of the interference materials on the meter output. However, even with such decreased oxygen concentration, the interference materials such as CO, $CO_2$, and NO still exist in the reduction atmosphere as they are, and consequently, it is impossible to completely remove the above-mentioned interference effect. Particularly at a low concentration of the measuring object component $SO_2$, the interference effect is remarkable.

On the contrary, according to the embodiment shown in FIG. 5 as discussed above, the interference components are effectively converted to non-interference materials in the presence of the reduction catalyst 72 in a reduction atmosphere. The converted non-interference materials such as $CH_4$ and $N_2$ never provide the interference to the flame light and therefore never affect the luminous intensity of the measuring object component. As a result, the interference contributing coefficient in FIG. 6 is 1.0, thereby, exhibiting a meter output which precisely corresponds to the concentration of the measured object component in the sample gas.

Figure 7:
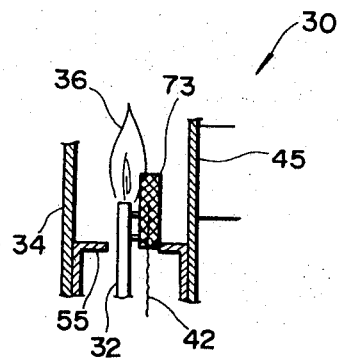
FIG. 7 is a schematic sectional view similar to FIG. 5 showing a modified example of the essential part of FIG. 5.

FIG. 7 shows a modified example of the second embodiment of the flame photometric detector analyzer according to the present invention, in which the tip of the sample gas introduction capillary tube 42 is covered with a catalyst 73 which may be positioned to contact the hydrogen rich flame 36 as shown.

Figure 8:
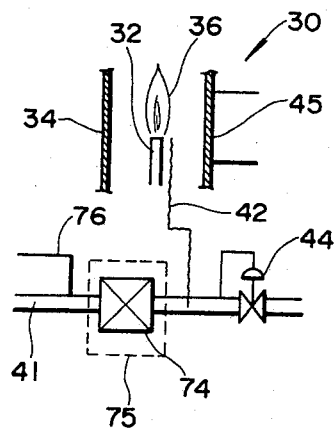
FIG. 8 is a schematic sectional view of an essential part of another modified example of the analyzer of FIG. 5.

FIG. 8 shows another modified example of the second embodiment of the analyzer, in which a catalyst cylinder 74 filled with reduction catalyst material is disposed in the sample gas supply line 41. The catalyst cylinder 74 is located within a high temperature box in which the temperature is maintained high and constant. The catalyst cylinder 74 is supplied with hydrogen gas in a suitable amount via a hydrogen gas supply pipe 76.

Figure 9:
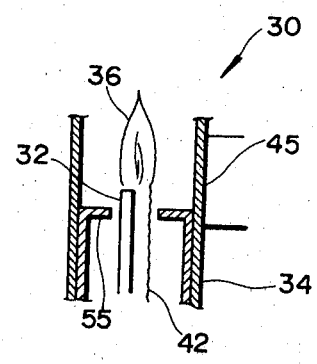
FIG. 9 is a schematic sectional view similar to FIG. 5 showing a further modified example of the analyzer of FIG. 5.

FIG. 9 shows a further modified example of the second embodiment of the analyzer, in which the sample gas introduction capillary tube 42 is formed of a catalytic material for promoting the reduction of the oxide components in the sample gas. Additionally, hydrogen gas is supplied into the capillary tube 42 with the sample gas, though not shown.

In these examples shown in FIGS. 8 and 9, the interference components CO, $CO_2$ and NO in the sample gas are reduced to be converted into non-interference components $CH_4$ and $N_2$ before being supplied to the hydrogen rich flame 36, and therefore these examples exhibit the same effect as in the arrangements shown in FIGS. 5 and 7. Additionally, in these examples, it is unnecessary to locate the catalyst in the vicinity of the hydrogen rich flame 36, which leads to an advantage in layout for the components of the analyzer.

It will be appreciated from the above, that according to the second embodiment of the present invention, the interference components in the sample gas are converted into non-interference substances in the presence of the catalyst and under hydrogen-reduction atmospheric condition, and therefore the luminous intensity of the measuring object component is not affected by or does not receive interference from the interference component in the sample gas, whereby the meter output can precisely reflect the detected measuring object component luminous intensity.

Figure 10:
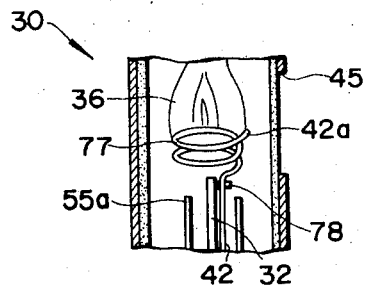
FIG. 10 is a schematic sectional view of the essential part of a third embodiment of the flame photometric detector analyzer in accordance with the present invention.

FIG. 10 illustrates a third embodiment of the flame photometric detector analyzer according to the present invention. In this embodiment, the sample gas introduction line or metering tube 42 extends toward the hydrogen rich flame 36 through an air nozzle 55a which is integral with the air guide 55. In this instance, the end section of the metering tube 42 serves as a heated section 77 located in the hydrogen rich flame 36 and formed into a shape for easily receiving heat from the flame 36. As shown, the heated section 77 is formed into a spiral shape. A supporting member 78 supports the metering tube 42 to the hydrogen nozzle 32. It is preferable to locate a sample gas ejection opening 42a at or in the vicinity of the window 45 through which flame light from the hydrogen rich flame passes to the optical filter 47, in order to facilitate detection of the flame light.

Figure 11:
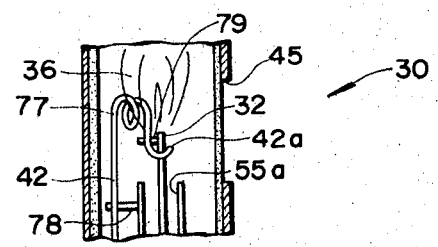
FIG. 11 is a schematic sectional view similar to FIG. 10 showing a modified example of the analyzer of FIG. 10.

FIG. 11 shows an arrangement similar to FIG. 10 with the exception that the spiral shaped heated section 77 of the metering tube 42 is located to contact the peripheral section of the flame 36. A supporting member 79 supports the end section of the sample gas metering tube 42 to the hydrogen nozzle 32.

With these arrangements, when the sample gas (exhaust gas in this instance) at, for example, about 120° C. is introduced into the heated section 77 of the metering tube 42, it receives heat from the flame 36 so that its temperature is raised to a level of 200° to 600° C. Accordingly, the density of the sample gas is greatly decreased. However, in this state, the density of the measuring object component in the sample gas is also decreased. The same number of molecules or atoms of a light generating component is necessary to obtain the same output level of the voltmeter 50, and accordingly, the above-mentioned decreased density of the measuring object component results in lowering the meter output level. In order to avoid this drawback, a larger amount of the sample gas is preferably supplied to compensate for such density decrease. This may be accomplished by operating the pressure regulator 44 to increase the flow rate of the sample gas flowing through the sample supply line 41.

Figure 12:
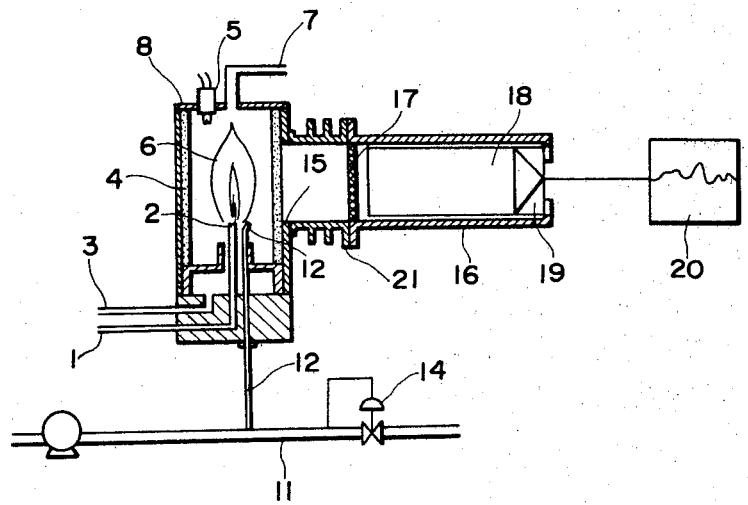
FIG. 12 is a diagrammatic sectional view of another conventional flame photometric detector analyzer.
Figure 13:
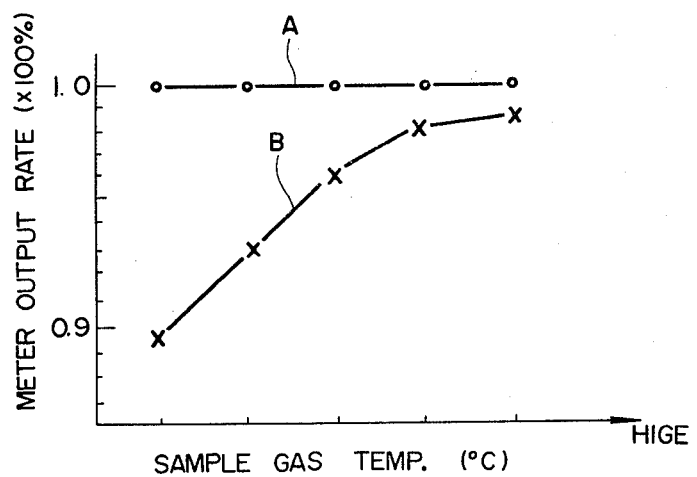
FIG. 13 is a graph showing the effect of the interference component on meter output in terms of temperature variation.
Figure 14:
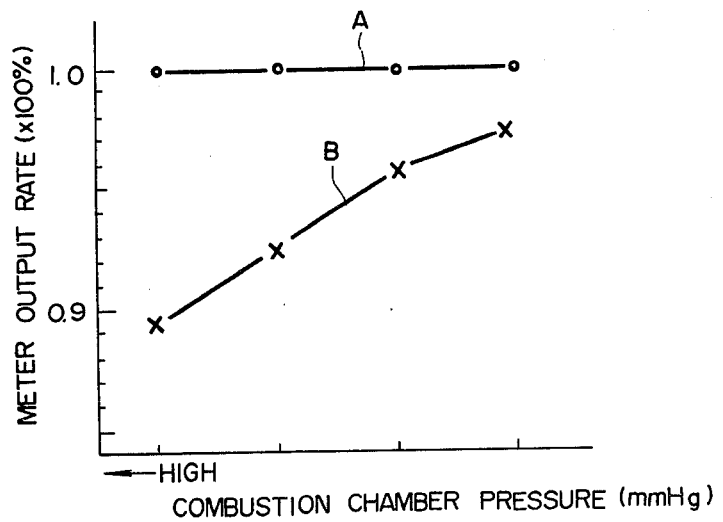
FIG. 14 is a graph similar to FIG. 13 showing the effect of the interference component on meter output in terms of pressure variation in the detector analyzer.

The advantageous effect obtained by the arrangements shown in FIGS. 10 and 11 will be explained hereinafter in comparison with a conventional corresponding flame photometric detector analyzer as shown in FIG. 12 wherein a heated section at the end section 12a of a sample gas metering tube (12) is not provided. FIG. 12 is similar to FIG. 1, and accordingly the same reference numerals designate the corresponding parts and elements. With such a conventional analyzer arrangement, it is known that as the density of the oxides such as $CO_2$, CO and NO in the exhaust gas or sample gas increases, the interference to the meter output increases. This will be apparent from FIGS. 13 and 14 where curve A indicates a case wherein 5 ppm of $SO_2$ exists in inert $N_2$ gas, and curve B indicates a case wherein 5 ppm of $SO_2$ exists in 1500 ppm of NO gas which greatly affects the flame light luminous intensity. That is, when the density of $SO_2$ is decreased by raising the temperature of the sample gas as shown in FIG. 13, and by decreasing the absolute pressure within the combustion chamber defined in the quartz glass cylinder 4 as shown in FIG. 12, it will become apparent that the accuracy in detected meter output decreases at a high density region of the interference component (NO), i.e., at a sample gas high temperature range and at a combustion chamber high pressure range.

However, according to the arrangement shown in FIGS. 10 and 11, the density of the interference components such as CO, $CO_2$ and NO is effectively decreased, and therefore the interference effect on the luminous intensity is decreased, thereby improving the measuring or detecting accuracy. Additionally, with the arrangements shown in FIGS. 10 and 11, the sample gas metering tube 42 is prevented from being cooled by air, thereby avoiding the increase in the interference effect due to an interference component density increase.

Figure 15:
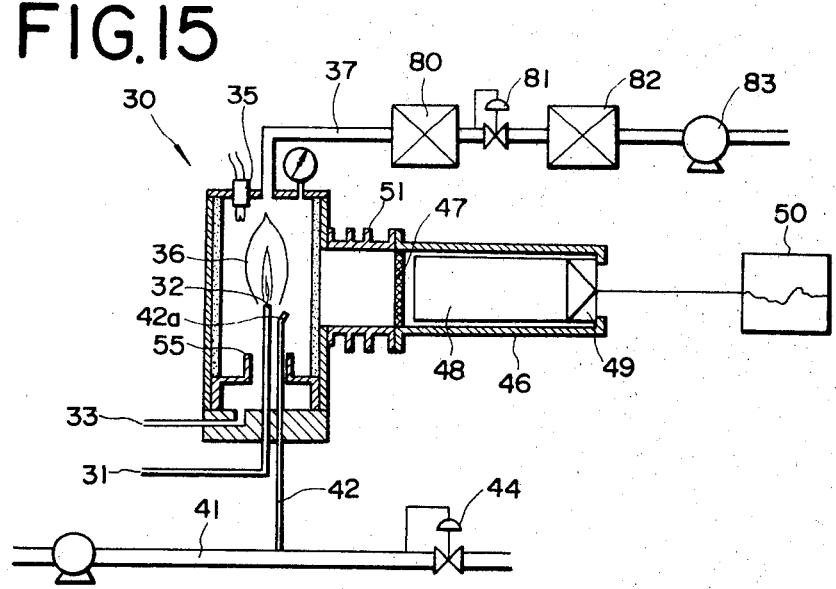
FIG. 15 is a further modified example of the third embodiment of the analyzer according to the present invention.

FIG. 15 shows a modified example of the third embodiment of the analyzer according to the present invention, which is arranged to decrease the density of the sample gas introduced into the hydrogen rich flame 36. In FIG. 15, a vacuum pump 83 is connected to the exhaust port 37 via a buffer tank 80, a constant pressure regulator 81 and another buffer tank 82 as shown, to decrease the pressure within the combustion chamber of the detector analyzer. It will be understood that the buffer tanks 80, 82 are used to remove the pulsation of the decreased pressure by the pump 83, which pulsation greatly affects the meter output.

With this arrangement, interference effect due to the interference components in the sample gas is suppressed by decreasing the density of the sample gas under a decreased pressure condition. Additionally, the sample gas ejection opening 42a can be located in the vicinity of the hydrogen rich flame 36, maintaining the end section of the sample gas metering tube 32 straight without the spiral section shown in FIGS. 10 and 11, and accordingly the metering tube can be shortened so that the sample gas reaches the flame 36 along the shortest distance. This improves the response in detecting the concentration of the measuring object component. This advantage is particularly effective for continuously quantitatively analyzing oxides of sulfur contained in exhaust gas discharged from an automotive internal combustion engine, which exhaust gas varies in its composition with lapse of time.

As appreciated from the above, according to the embodiments shown in FIGS. 10, 11 and 15, the density of the interference components such as CO, $CO_2$ and NO coexisting with the measuring object component in the sample gas is effectively decreased by heating the sample gas and by reducing the pressure within the combustion chamber of the analyzer, and therefore the luminous intensity of the flame light from the measuring object component does not receive the interference effect caused by the coexisting interference components.

Figure 16:
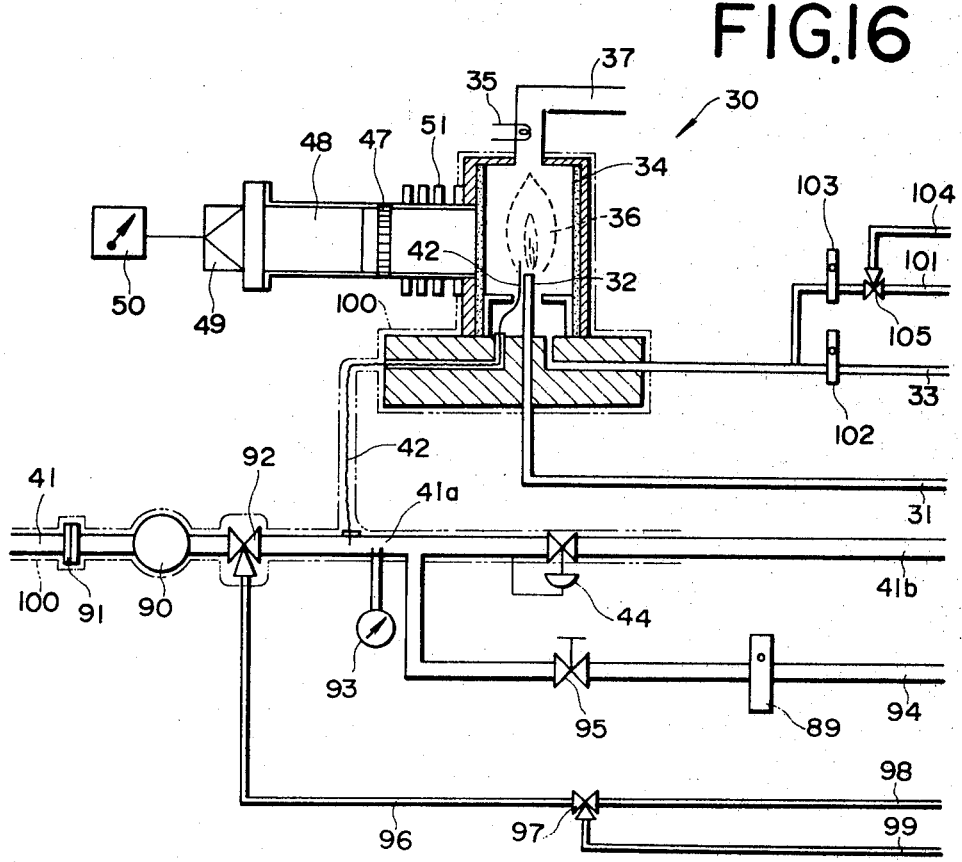
FIG. 16 is a diagrammatic illustration, partly in section, of a fourth embodiment of the flame photometric detector analyzer in accordance with the present invention.

FIG. 16 illustrates a fourth embodiment of the flame photometric detector analyzer in accordance with the present invention. In this embodiment, the sample supply line 41 is provided with a sample gas supply pump 90 for pressurizing sample gas, and further provided with a filter 91 for removing mist in the sample gas. The sample gas from the pump 90 is supplied via a three-way electromagnetic valve 92 into the sample gas introduction line 42. A sample gas pressure gauge 93 is provided downstream of the sample gas introduction line 42, to measure the pressure of the sample gas at a sample gas introduction section 41a defined upstream of the constant pressure regulator 44. A part of the sample gas passed through the constant pressure regulator 44 is discharged through a discharge section 41b.

A sample gas bypass passage 94 branches off from the sample gas introduction section 41a between the sample gas pressure gauge 93 and the constant pressure regulator 44. The sample gas bypass passage 94 is provided with a flow amount control valve 95 and a bypass flow amount measuring meter 89, so that the actual sample gas supply amount is controllable by regulating the bypass flow amount and pressure thereby.

The three-way electromagnetic valve 92 is connected via a passage 96 to another three-way electromagnetic valve 97 to which a zero gas supply line 98 and a span gas supply line 99 are connected. Accordingly, zero gas and span gas are selectively supplied through the valve 97 to the passage 96, and then either the zero gas, the span gas or the sample gas passing through the sample supply line 41 upstream of the valve 92 is selectively supplied to the sample gas introduction section 41a to be selectively introduced into the sample gas introduction line 42. It will be understood that the zero gas is a standard or calibration gas used to set the zero point. In this instance, pure $N_2$ gas is used as the zero gas. It will be also understood that the span gas is also a calibration gas used to set an upscale standardization point. As shown, the sample supply line 41 and the sample gas introduction line 42 are covered with a heating device 100 for heating the sample gas to be supplied to the flame 36 at a temperature from 120° to 200° C.

Additionally, in this embodiment, a pure nitrogen supply passage 101 is connected to the combustion supporting gas supply line 33 downstream of a flow amount measuring meter 102. Pure nitrogen gas from the supply line 101 is introduced to air flowing through the line 33 to dilute the air supplied to the vicinity of the flame 36, after its flow amount is measured by meter 103. An interference gas supply passage 104 is connected via a three-way electromagnetic valve 105 to the pure nitrogen gas supply passage 101 to introduce interference gas into the combustion supporting gas supply line 33. The interference gas is a gas which does not contain the measuring object component and has a certain concentration. Such a gas is, for example, $CO_2$, CO, NO, or HC which coexists in the sample gas or exhaust gas, and is capable of providing interference onto the luminous intensity of the flame emitted from the measuring object component.

In operation, prior to the analysis of the sample gas, the supply of the sample gas, for example a mixed gas containing $SO_2$, is stopped by operating the three-way electromagnetic valves 92, 97 in order to supply the standard gas (zero gas; pure nitrogen gas) to the sample gas introduction line 42. At this time, the pressure regulator valve 44 or the bypass flow amount controlling valve 95 are operated to obtain a certain pressure of the sample gas in the sample gas introduction section 41a depending upon previously determined pressure and flow amount characteristics. In this state, the output resulting from the flame light emitted from the zero gas in the hydrogen rich flame 36 is measured by the voltmeter 50, this output being referred to as "dark current". The output due to this dark current of the meter 50 is electrically cancelled, and then the output of the meter at this time is calibrated to set the zero point of the meter output.

Subsequently, a certain amount of the interference gas is mixed with the combustion supporting gas and then introduced into the hydrogen rich flame 36. At this time, due to the electric current generated by the flame light from the interference gas, the meter output on which the zero point is set is raised, this raised outlet value being referred to as "adjustment value of dark current". This adjustment value is at a constant level and is amplified depending the on amplification rate of the amplifier 49, if the state of the flame 36 is constant. Thus, prior to the initiation of the sample gas analysis, the zero gas is supplied in the same amount as that of the sample gas, introducing the certain amount of the interference gas into the hydrogen rich flame to measure the dark current which serves as a standard.

Next, the three-way electromagnetic valve 105 is operated to change the flow passage to stop the supply of the interference gas, and additionally the three-way electromagnetic valve 92 is operated to change the flow path to stop the supply of the zero gas and to initiate introduction of the sample gas. The flow amount of the sample gas flowing through the sample gas introduction line 42 is proportional to the pressure in the sample gas introduction section 41a of the supply line 41. The pressure value in the introduction section 41a is set at the same level as during zero gas introduction. Therefore, a predetermined sample introduction amount can be obtained at a period of initiation of the sample gas analysis.

Figure 17:
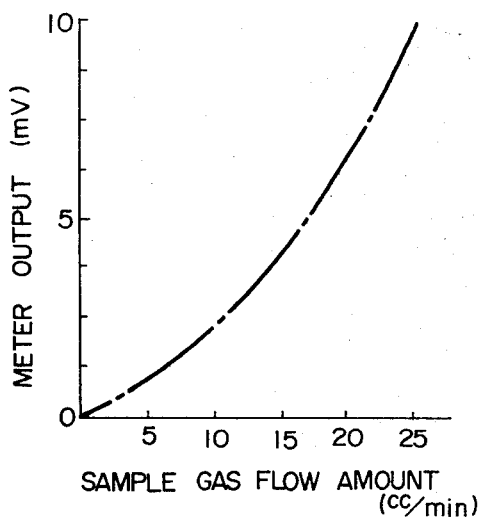
FIG. 17 is a graph showing the variation in meter output in terms of variation in the flow amount of the sample gas.

During the sample gas analysis thus initiated, when mist attaches onto the inner surface of the sample gas introduction line 42, the effective sectional area of the line 42 decreases and therefore the sample gas flow amount decreases. When the sample gas flow amount decreases, the output of the meter 50 decreases even if the concentration of the measuring object component is the same, as clearly shown in FIG. 17.

In this regard, the flow amount measuring in the sample gas introduction line 42 will be carried out as follows: At first, the zero gas is supplied into the sample gas introduction gas line 42 in place of the sample gas, and thereafter the interference gas is introduced in the same amount as that in the previous operation for obtaining the adjustment value of dark current, into the combustion supporting gas to measure an adjustment value of dark current. If no mist is attached and accordingly no variation in sample gas flow amount occurs, this adjustment value is the same level as that of the previously measured adjustment value of dark current. In this state, the same pressure in the sample gas introduction section 41a is maintained to continue the operation of the sample gas analysis.

On the contrary, when the flow amount of sample gas decreases due to mist attaching, the zero point of the adjustment value relatively lowers and therefore the adjustment value indicated by the meter 50 lowers, even though the dark current due to the interference gas is the same. In this state, the pressure in the sample gas introduction section 41a is raised to the value of the previously or initially measured adjustment value of the dark current by varying the set value of the constant pressure regulator 44 or by controlling the bypass flow amount control valve 95. It will be understood that even if the effective sectional area of the sample gas introduction line 42 decreases, the decreased amount of the sample gas can be compensated for by raising the pressure in the sample gas introduction section 14a. By thus controlling the pressure, it becomes possible to indirectly regulate the sample gas flow amount to a set value.

The advantage gained by the arrangement shown in FIG. 16 will be explained hereinafter in comparison with a conventional flame photometric detector analyzer shown in FIG. 18 which is similar to the arrangement in FIG. 16, and accordingly the corresponding parts and elements are designated by the same reference numerals.

Figure 18:
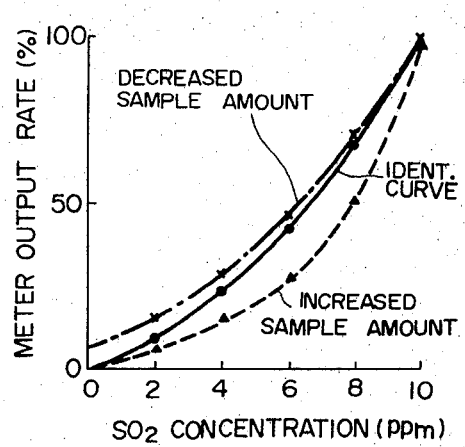
FIG. 18 is a graph showing meter output difference depending upon different sample gas amounts, in terms of $SO_2$ concentration.

As stated above, it is necessary to control the flow amount of the sample gas to a constant value since a sample gas flow amount variation leads to a variation in the meter output relative to the same concentration of the measuring object component as shown in FIG. 18. This results from the fact that the effect of the interference component coexisting the measuring object component in the sample gas varies with the increase or decrease in the sample gas flow amount.

In the usual operation of conventional analyzers, although the filter 91 is provided upstream of the pump 90 to remove the mist in the sample gas, the mist passed through the filter 91 attaches onto the inner surface of the sample gas introduction line 42 or tube since the inner diameter of the tube 42 is small, for example, 0.2 mm. Accordingly, the accumulation of such mist in the tube 42 by long term use leads to a variation in flow amount of the sample gas, which will result in an analytical error.

In this regard, in the operation of the conventional analyzer shown in FIG. 18, in order to maintain a constant flow amount of the sample gas, the sample supply line 11, etc. are periodically disassembled and then the relationship between the pressure and the flow amount in the sample gas introduction section 11a is again measured, thereby operating the constant pressure regulator 14 or the flow amount control valve 95 to obtain a predetermined flow amount of the sample gas.

However, by this method, such disassembling the analyzer prolongs the stop time duration in analytical operation of the analyzer, and besides the disassembly operation is very troublesome. Additionally, even if the pressure and flow amount characteristics have been varied, the causes thereof can not easily judged until the disassembly is carried out. Accordingly, it is necessary to periodically disassemble the analyzer for reasons in addition to cleaning the mist accumulation from the inside of the tube 42.

Figure 19:
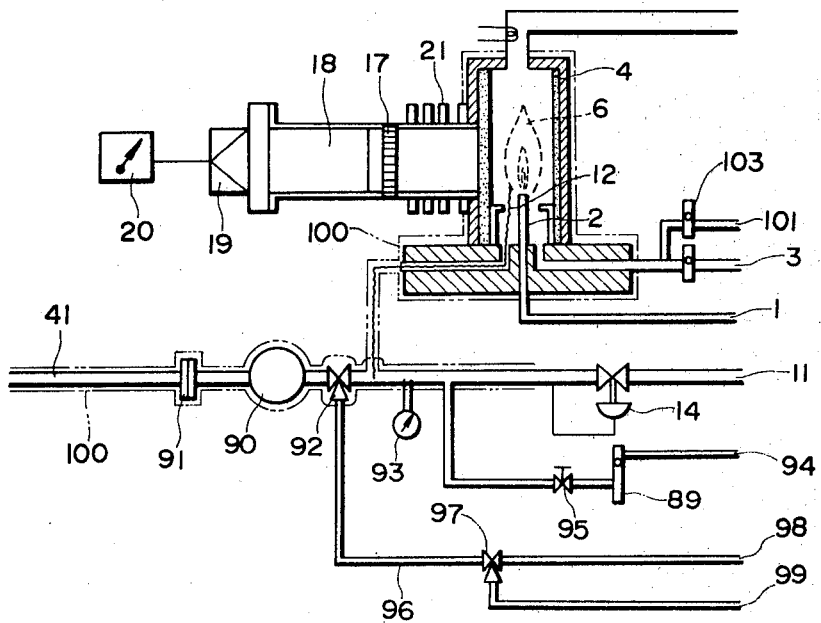
FIG. 19 is a diagrammatic illustration, partly in section of a further conventional flame photometric detector analyzer.

It will be appreciated from the above, according to the embodiment shown in FIG. 16, it is unnecessary to disassemble the analyzer to measure again the flow amount of the sample gas, and therefore the adjustment of sample gas flow amount can be easily achieved without disassembling the analyzer. Therefore, the arrangement of the analyzer shown in FIG. 16 can overcome the serious drawbacks encountered in the conventional similar analyzer shown in FIG. 19. As appreciated from the above, according to the embodiment shown in FIG. 16, the checking and adjustment of the sample gas flow amount can be easily achieved by introducing the interference gas with reference to the adjustment value of dark current. Therefore, accurate adjustment of the sample gas supply can be easily achieved and is not troublesome as compared with the conventional analyzer.

Figure 20:
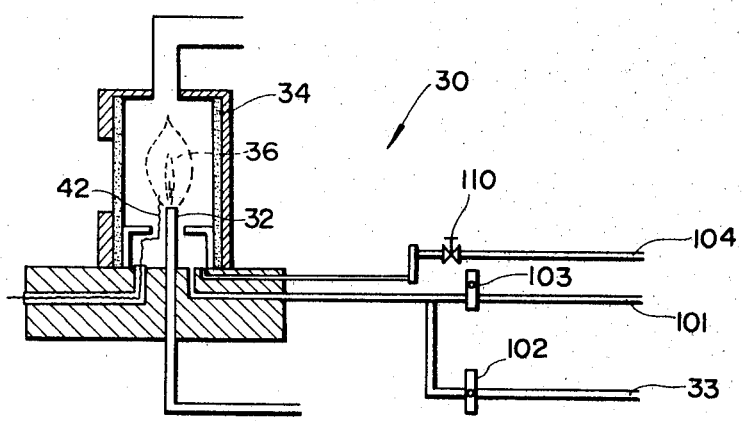
FIG. 20 is a diagrammatic view of a modified example of the second embodiment of the analyzer of FIG. 16.

FIG. 20 shows a modified example of the fourth embodiment of the analyzer according to the present invention, in which the interference gas passage 104 is disposed to open to the inside of the combustion chamber defined inside the quartz glass cylinder 38 so that the interference gas is directly introduced into the combustion chamber after its amount is regulated by a flow amount regulator 110.

Figure 21:
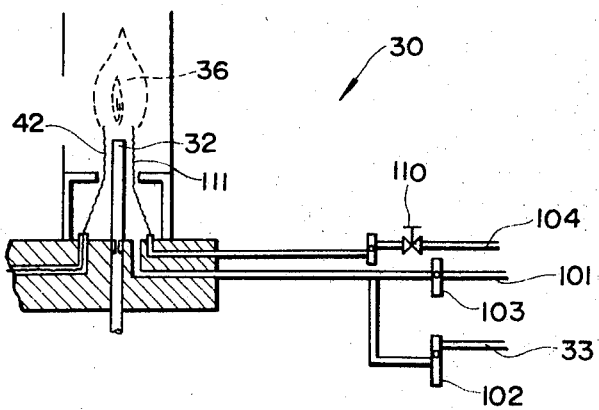
FIG. 21 is a diagrammatic illustration similar to FIG. 20 showing another modified example of the analyzer of FIG. 16.

FIG. 21 shows another modified example of the embodiment of the analyzer shown in FIG. 20, in which an interference gas ejection tube 111 is connected to the end of the interference gas supply passage 104. The tip of the ejection tube 111 is positioned to reach the hydrogen rich flame 36 to directly introduce the interference gas into the flame 36. It will be appreciated that both arrangements shown in FIGS. 20 and 21 exhibit the same advantageous effect as in the arrangement in FIG. 16.

While the background providing device 60 has been shown and described as being provided only in the first embodiment and the modifications thereof, it will be understood that the background providing device is, as a matter of course, provided to all the other embodiments shown in FIGS. 5 to 21.

Although the exhaust gas from the automotive internal combustion engine has been described as being used as the sample gas, it will be appreciated that other gases containing a flame generating component are usable as the sample gas to be supplied to the flame photometric detector analyzer.

What is claimed is:
1. A flame photometric detector analyzer, comprising:
   means defining and containing a source of fuel gas and including a first conduit means through which said fuel gas flows;
   a fuel gas discharge nozzle connected to said first conduit means to be supplied with the fuel gas to form a flame when ignited,
   means defining and containing a source of combustion supporting gas and including a second conduit means through which said combustion supporting gas is supplied to the vicinity of the tip of said fuel gas discharge nozzle to assist the combustion of fuel gas discharged from said nozzle;
   means defining and containing a source of sample gas and including a third conduit means through which said sample gas is supplied to the flame, said sample gas containing a measuring object component to be detected;
   means defining and containing a source of background component gas and including a background providing means for supplying to the flame, simultaneously with the sample gas from said third conduit means said background component gas capable of emitting a characteristic light spectrum having the same wave length as that of the characteristic light spectrum of the measuring object component;
   photodetector means responsive to photoemission from the mixture of said measuring object component and said background component during operation of said analyzer;
   means defining and containing a source of standard gas and including a means for supplying said standard gas into the flame through said third conduit means, said standard gas having a concentration of a component and being capable of generating a dark current in said photodetector means;
   means defining and containing a source of interference gas including a means for supplying said interference gas into the flame, said interference gas being capable of varying the dark current; and
   means for controlling the pressure of the sample gas to be supplied through said third conduit means to the flame with reference to the variation of the dark current, to regulate the amount of the sample gas to be supplied to the flame.
2. A flame photometric detector analyzer, comprising:
   first conduit means through which a fuel gas flows;
   a fuel gas discharge nozzle connected to said first conduit means to be supplied with the fuel gas to form a flame when ignited;
   second conduit means through which a combustion supporting gas is supplied to the vicinity of the tip of said fuel gas discharge nozzle to assist the combustion of fuel gas discharged from said nozzle;
   third conduit means through which a sample gas is supplied to the flame, said sample gas containing a measuring object component to be detected;
   background providing means for supplying to the flame, simultaneously with the sample gas from said third conduit means, a background component gas capable of emitting a characteristic light spectrum having the same wave length as that of the characteristic light spectrum of the measuring object component;
   photodetector means responsive to photoemission from the mixture of said measuring object component and said background component during operation of said detector; and
   means for decreasing the density of the sample gas to be introduced into the flame formed at said fuel gas discharge nozzle, said density decreasing means including means for decreasing the pressure within a combustion chamber of said analyzer, said fuel gas discharge nozzle and said sample gas introduction tube being located within said combustion chamber.
3. A flame photometric detector analyzer as claimed in claim 2, wherein said pressure decreasing means includes a vacuum pump communicating with said combustion chamber.
4. A flame photometric detector analyzer as claimed in claim 2, wherein said pressure decreasing means fur- ther comprises a constant pressure regulator in a vacuum supply line connected to said combustion chamber, located downstream of said vacuum pump, and first and second buffer tanks disposed in said vacuum supply line and located downstream and upstream of said pressure regulator, respectively.

5. A flame photometric detector analyzer as claimed in claim 2, further comprising means for increasing the amount of the sample gas to be supplied to the flame.

6. A flame photometric detector analyzer as claimed in claim 5, wherein said sample gas amount increasing means includes a pressure regulator located in said sample supply line.

7. A flame photometric detector analyzer, comprising:
means defining and containing a source of fuel gas and including a first conduit means through which said fuel gas flows;
a fuel gas discharge nozzle connected to said first conduit means to be supplied with the fuel gas to form a flame when ignited;
means defining and containing a source of combustion supporting gas and including a second conduit means through which said combustion supporting gas is supplied to the vicinity of the tip of said fuel gas discharge nozzle to assist the combustion of fuel gas discharged from said nozzle;
means defining and containing a source of sample gas and including a third conduit means through which said sample gas is supplied to the flame, said sample gas containing a measuring object component to be detected, said third conduit means including a sample supply line through which said sample gas flows, and a sample gas introduction tube whose one end is connected to said sample supply line and whose other end is positioned in the vicinity of the tip of said fuel gas discharge nozzle to directly introduce the sample gas into the flame;
means defining and containing a source of background component gas and including a background providing means for supplying to the flame, simultaneously with the sample gas from said third conduit means said background component gas capable of emitting a characteristic light spectrum having the same wave length as that of the characteristic light spectrum of the measuring object component, said background providing means including a background component gas supply line through which background component gas flows, and a background component gas introduction tube connected to said background gas supply line, the background component gas being introduced into said flame formed at the tip of said fuel gas discharge nozzle;
photodetector means responsive to photoemission from the mixture of said measuring object component and said background component during operation of said analyzer;
means defining and containing a source of a standard gas and including a means for supplying said standard gas into the flame through said third conduit means, said standard gas having a concentration of a component and being capable of generating a dark current in said photodetector means;
means defining and containing a source of an interference gas and including a means for supplying said interference gas into the flame, said interference gas being capable of varying the dark current; and
means for controlling the pressure of the sample gas to be supplied through said third conduit means to the flame with reference to the variation of the dark current, to regulate the amount of the sample gas to be supplied to the flame.

8. A flame photometric detector analyzer as claimed in claim 7, wherein said interference gas supply means includes interference gas supply conduit means through which interference gas is selectively supplied to said second conduit means.

9. A flame photometric detector analyzer as claimed in claim 7, wherein said interference gas has a concentration of an interference component contained in the sample gas and is different from the measuring object component in the sample gas.

10. A flame photometric detector analyzer as claimed in claim 9, wherein said standard gas is pure nitrogen gas.

11. A flame photometric detector analyzer as claimed in claim 7, wherein said interference gas supply means includes interference gas supply conduit means connected to a combustion chamber within which said flame is formed to directly introduce the interference gas into the combustion chamber.

12. A flame photometric detector analyzer as claimed in claim 11, said interference gas supply conduit means includes an interference gas introduction tube whose one end is positioned in the vicinity of the tip of said fuel gas discharge nozzle to directly supply the interference gas into the flame.

13. A flame photometric detector analyzer as claimed in claim 7, wherein said third conduit means further includes a bypass conduit branched off from a first section downstream of a second section to which said sample gas introduction tube is connected.

14. A flame photometric detector analyzer as claimed in claim 13, wherein said sample gas pressure controlling means includes a pressure regulator disposed in said third conduit means downstream of said first section, and a flow control valve disposed in said bypass conduit.

15. A flame photometric detector analyzer for continuously detecting concentration of $SO_2$ contained in the exhaust gas discharged from an automotive internal combustion engine during its operation, said analyzer comprising:
means defining and containing a source of hydrogen gas and including a first conduit means through which said hydrogen gas is supplied;
a burner jet connected to said first conduit means to be supplied with said hydrogen gas to form a hydrogen rich flame at the tip of said burner jet, when ignited by igniting means;
means defining and containing a source of air and including a second conduit means through which said air is supplied to the vicinity of the tip of said burner jet to assist the combustion of hydrogen gas discharged from the burner jet tip;
third conduit means through which the exhaust gas from said internal combustion engine is supplied to the hydrogen rich flame, said exhaust gas containing $SO_2$ to be detected;
means for providing a predetermined amount of $SO_2$ gas simultaneously with said exhaust gas from said third conduit, to the hydrogen rich flame;
photodetector means responsive to photoemission from the mixture of $SO_2$ in the exhaust gas and from said SO$_2$ providing means during operation of said analyzer;

said photodetector means responsive to the photoemission from the mixture of said measuring object component and said background component during operation of said analyzer;

means defining and containing a source of a standard gas and including means for supplying said standard gas into the flame through said third conduit means, said standard gas having a concentration of a component and being capable of generating a dark current in said photodetector means;

means defining and containing a source of an interference gas and including means for supplying said interference gas into the flame, said interference gas being capable of varying the dark current; and means for controlling the pressure of the sample gas to be supplied through said third conduit means to the flame with reference to the variation of the dark current, to regulate the amount of the sample gas to be supplied to the flame.

16. A flame photometric detector analyzer, comprising:

a first conduit means through which a fuel gas flows, said fuel gas being hydrogen gas;

a fuel gas discharge nozzle connected to said first conduit means to be supplied with the fuel gas to form a flame when ignited, said flame being hydrogen rich flame;

second conduit means through which a combustion supporting gas is supplied to the vicinity of the tip of said fuel gas discharge nozzle to assist the combustion of fuel gas discharged from said nozzle;

third conduit means through which a sample gas is supplied to the flame, said sample gas containing a measuring object component to be detected, said third conduit means including a sample supply line through which said sample gas flows, and a sample gas introduction tube whose one end is connected to said sample supply line and whose other end is positioned in the vicinity of the tip of said fuel gas discharge nozzle to directly introduce the sample gas into the flame;

background providing means for supplying to the flame, simultaneously with the sample gas from said third conduit means, a background component gas capable of emitting a characteristic light spectrum having the same wave length as that of the characteristic light spectrum of the measuring object component, said background providing means including a background component gas supply line through which background component gas flows, and a background component gas introduction tube connected to said background gas supply line, the background component gas being introduced into said flame formed at the tip of said fuel gas discharge nozzle;

photodetector means responsive to photoemission from the mixture of said measuring object component and said background component during operation of said detector; and means for decreasing the density of said sample gas to be introduced into the flame formed at the tip of said fuel gas discharge nozzle, said density decreasing means including a heatable section forming part of said sample gas introduction line, which heatable section is heatable by the flame formed at the tip of said fuel gas discharge nozzle, said heatable section being located to contact the flame and being formed into a spiral shape to increase the heat receiving surface area through which the heat of the flame is transmitted.

* * * * *